United States Patent
Wiederin

(10) Patent No.: US 10,661,283 B1
(45) Date of Patent: May 26, 2020

(54) TREATED NEBULIZER TIP AND SPRAY CHAMBER

(71) Applicant: Elemental Scientific, Inc., Omaha, NE (US)

(72) Inventor: Daniel R. Wiederin, Omaha, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 197 days.

(21) Appl. No.: 15/187,082

(22) Filed: Jun. 20, 2016

Related U.S. Application Data

(60) Provisional application No. 62/181,671, filed on Jun. 18, 2015.

(51) Int. Cl.
| | |
|---|---|
| *A61M 11/00* | (2006.01) |
| *B05B 1/02* | (2006.01) |
| *B05B 9/01* | (2006.01) |
| *B05B 15/55* | (2018.01) |
| *A61M 11/06* | (2006.01) |
| *A61M 15/00* | (2006.01) |

(52) U.S. Cl.
CPC ............. *B05B 1/02* (2013.01); *A61M 11/06* (2013.01); *B05B 9/01* (2013.01); *B05B 15/55* (2018.02); *A61M 15/00* (2013.01)

(58) Field of Classification Search
CPC ....... A61M 11/06; A61M 15/00; B05B 15/55; B05B 9/01; B05B 1/02; B05B 7/0012
USPC ........................................ 128/200.14, 200.18
See application file for complete search history.

(56) References Cited

U.S. PATENT DOCUMENTS

| | | | | |
|---|---|---|---|---|
| 5,054,478 A | * | 10/1991 | Grychowski | A61M 16/16 128/200.14 |
| 5,660,167 A | * | 8/1997 | Ryder | A61M 11/06 128/200.14 |
| 6,328,030 B1 | * | 12/2001 | Kidwell | A61M 16/08 128/200.21 |
| 7,814,902 B2 | * | 10/2010 | Abrams | A61M 11/02 128/200.14 |
| 2003/0127538 A1 | * | 7/2003 | Patel | A61M 15/0065 239/338 |
| 2007/0137648 A1 | * | 6/2007 | Addington | A61M 11/06 128/204.25 |
| 2008/0233053 A1 | * | 9/2008 | Gross | A61K 9/0048 514/1.1 |

(Continued)

*Primary Examiner* — Alex M Valvis
(74) *Attorney, Agent, or Firm* — Kevin E. West; Advent, LLP

(57) ABSTRACT

A system can include a nebulizer having a tip and a spray chamber configured to be in fluid communication with the nebulizer. The tip of the nebulizer and/or an interior of the spray chamber can have a treated surface. The nebulizer and/or the spray chamber can be treated using a physical abrasion technique, chemically etched, and so forth. In some embodiments, treated surfaces of the nebulizer and the spray chamber can be proximate to one another. The spray chamber can include a drain ridge, which can project into an interior of the spray chamber, be depressed away from an interior of the spray chamber, and/or include a treated surface. The spray chamber can also include an output port having a treated surface. In some embodiments, the output port can include an additional port so that rinse liquid can flow through the spray chamber (e.g., continuously and/or intermittently).

13 Claims, 9 Drawing Sheets

(56) References Cited

U.S. PATENT DOCUMENTS

Figure 1:
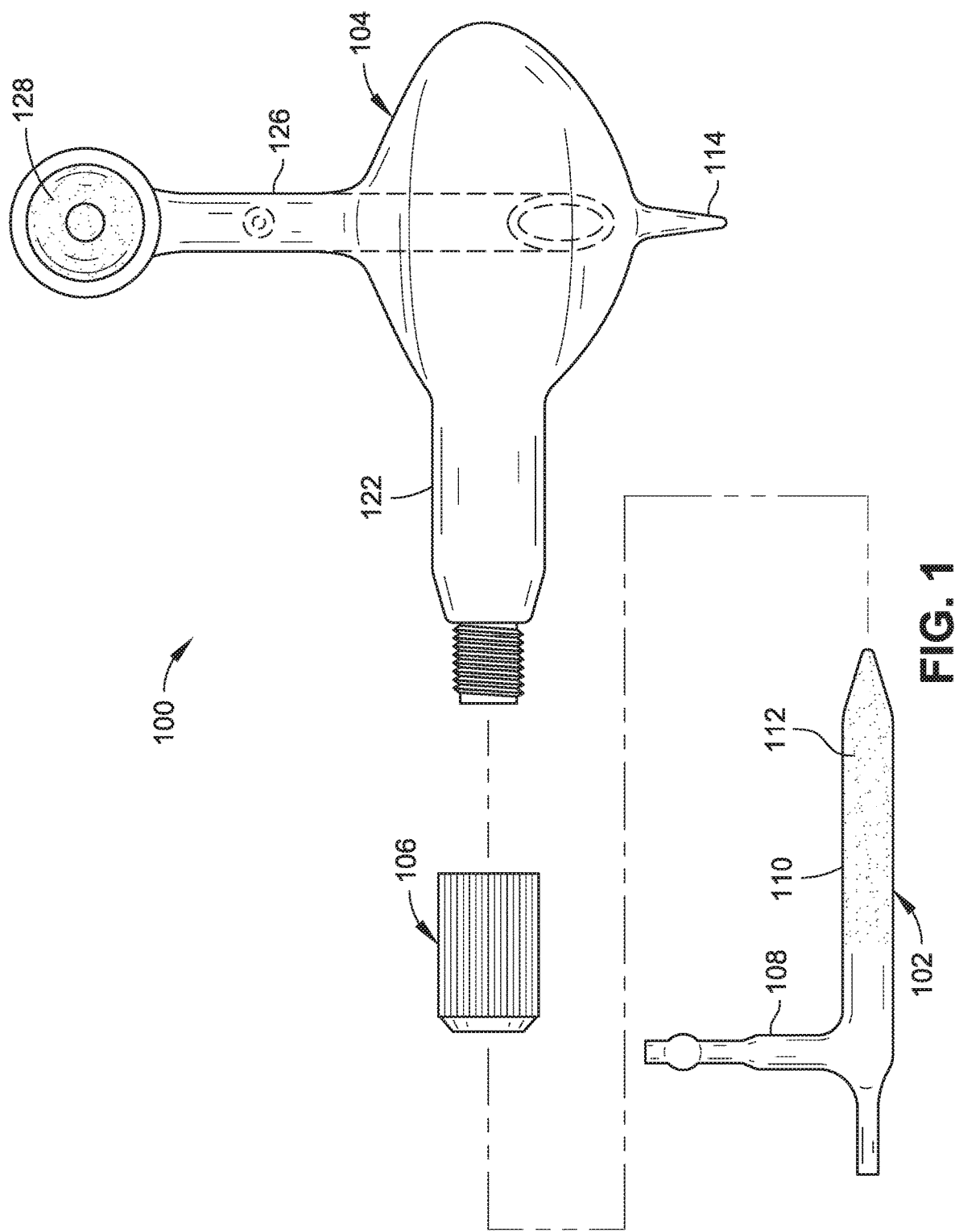
Figure 2:
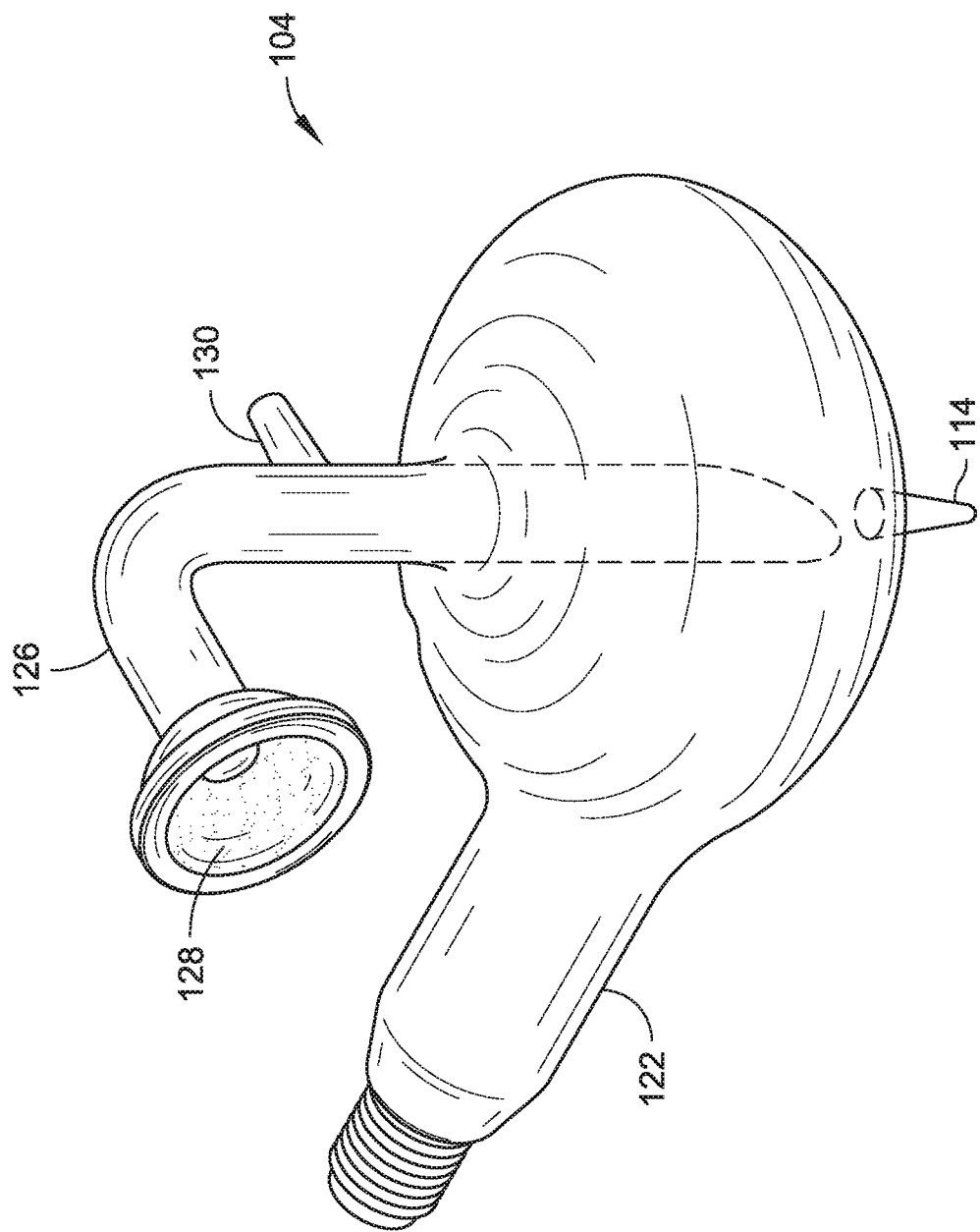
Figure 3:
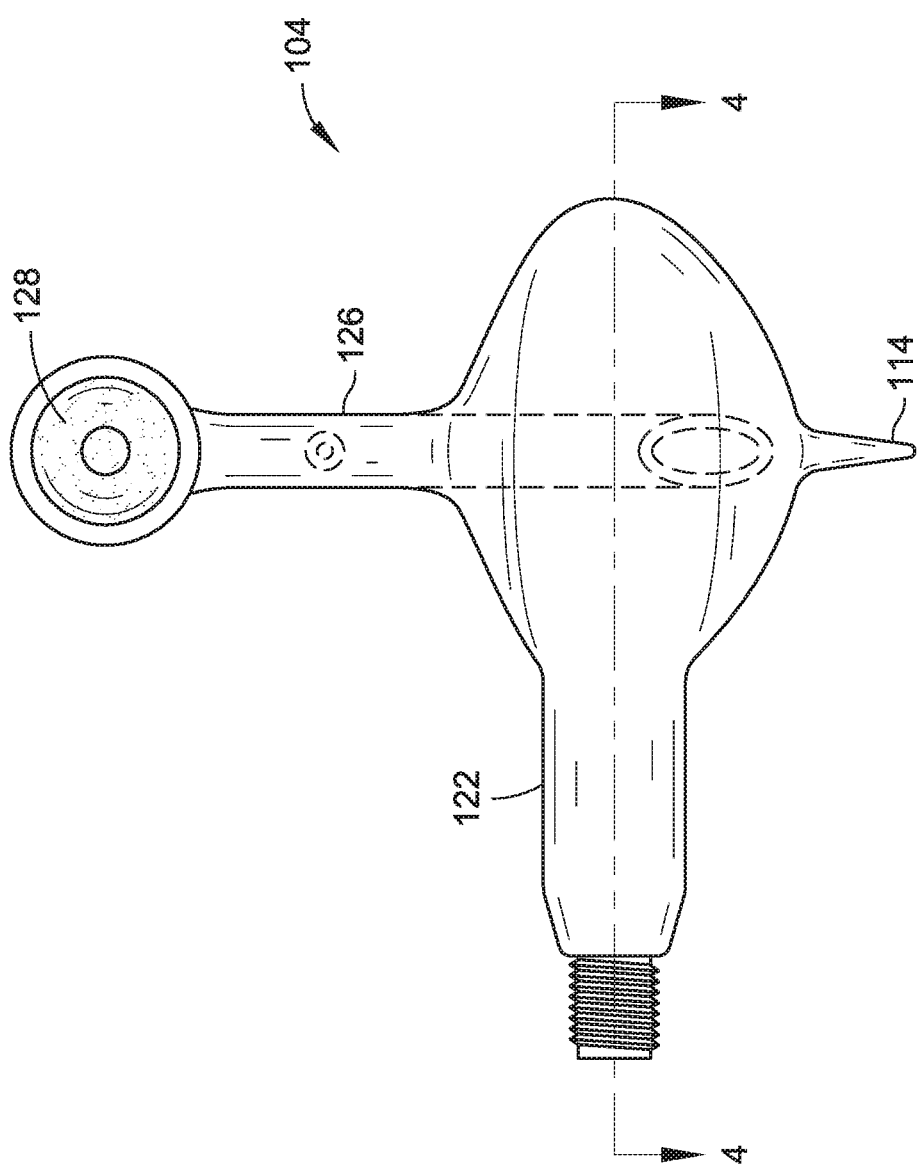
Figure 4:
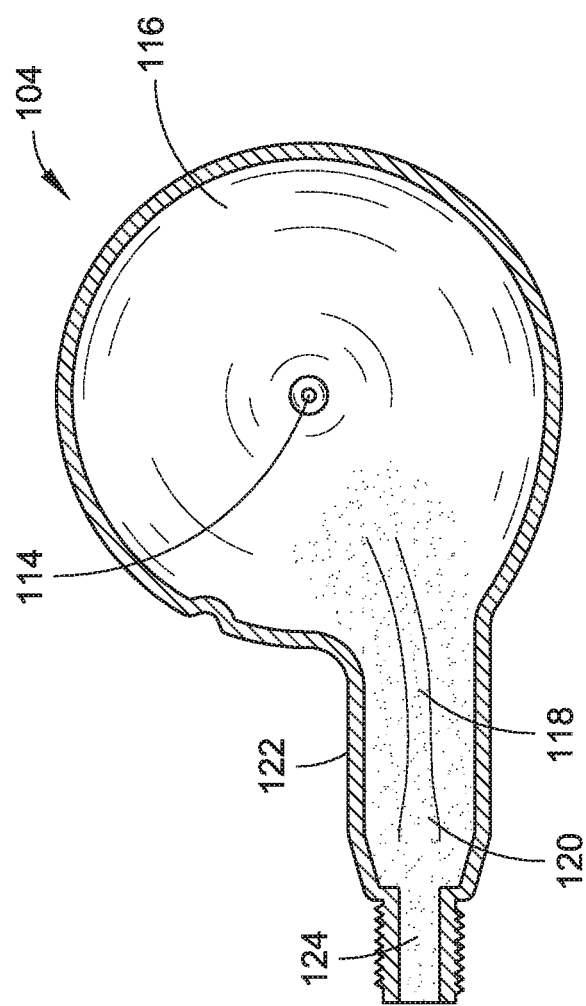
Figure 5:
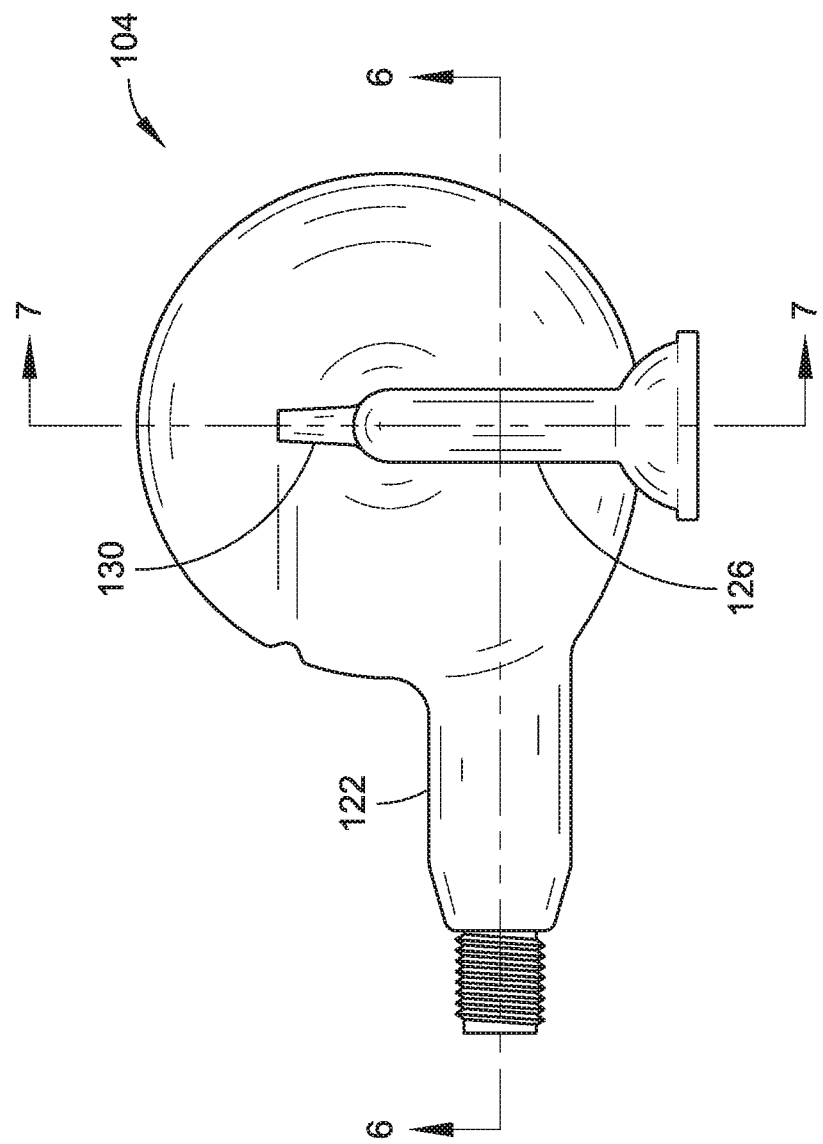
Figure 6:
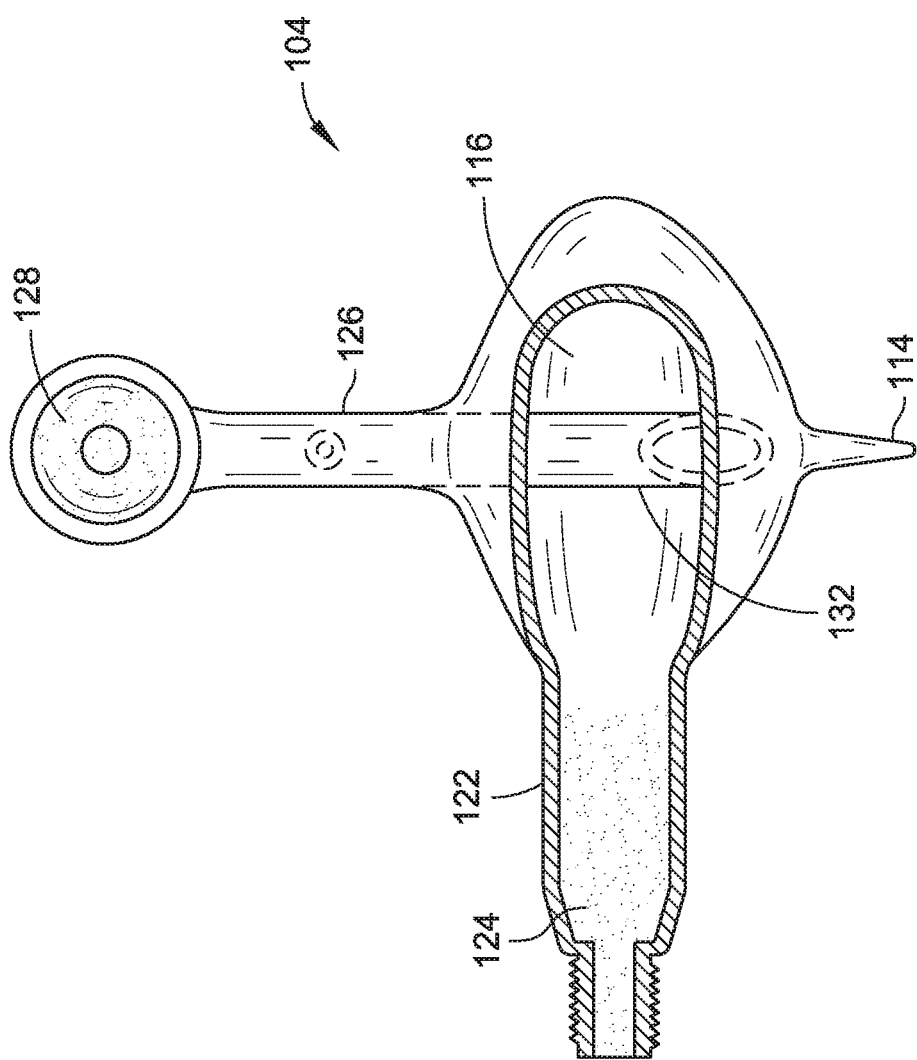
Figure 7:
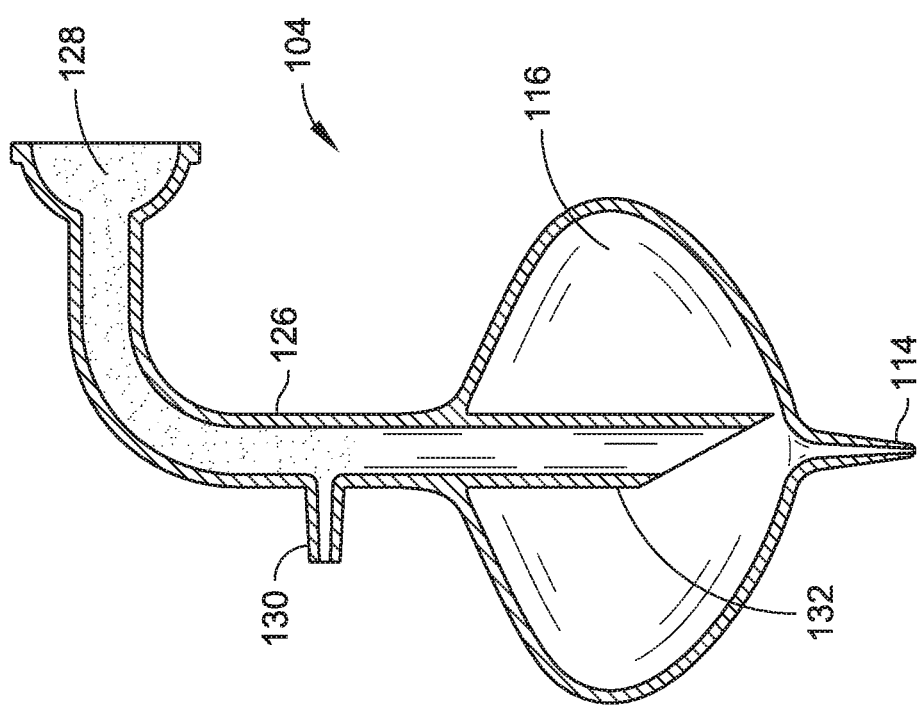
Figure 8:
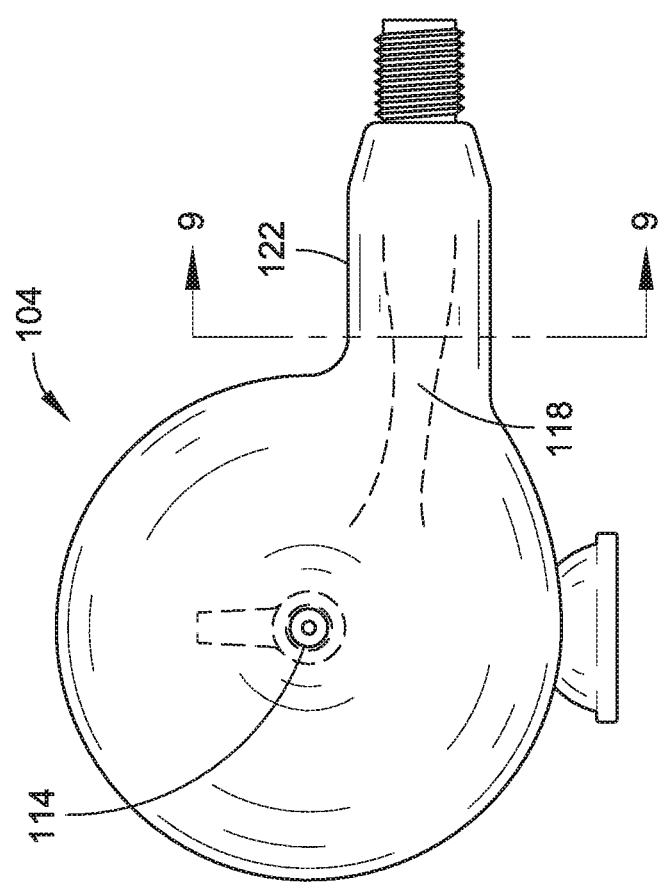
Figure 9:
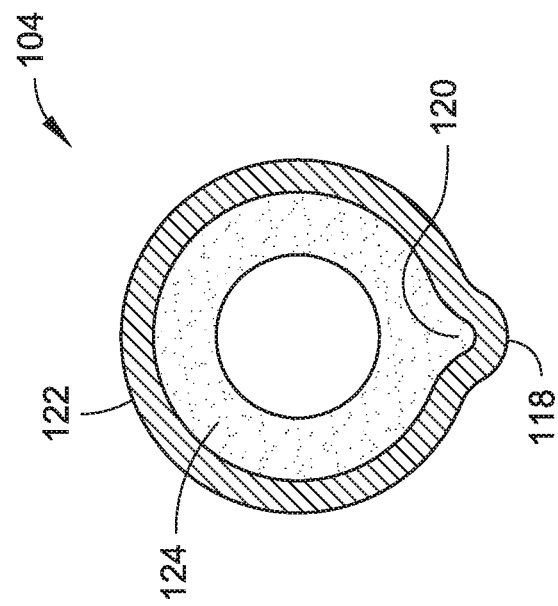

2009/0194099 A1* 8/2009 Kladders ............ A61M 15/0065
128/200.14
2015/0101597 A1* 4/2015 Boucher ............... A61M 16/16
128/200.18

* cited by examiner

TREATED NEBULIZER TIP AND SPRAY CHAMBER

CROSS-REFERENCE TO RELATED APPLICATIONS

The present application claims the benefit under 35 U.S.C. § 119(e) of U.S. Provisional Application Ser. No. 62/181,671, filed Jun. 18, 2015, and titled "TREATED NEBULIZER TIP AND SPRAY CHAMBER," which is herein incorporated by reference in its entirety.

BACKGROUND

A spray chamber can be used to remove liquid droplets, which may be produced by, for example, a nebulizer connected to the spray chamber.

SUMMARY

A system can include a nebulizer having a tip and a spray chamber configured to be in fluid communication with the nebulizer. The tip of the nebulizer and/or an interior of the spray chamber can have a treated surface. The nebulizer and/or the spray chamber can be treated using a physical abrasion technique, chemically etched, and so forth. In some embodiments, treated surfaces of the nebulizer and the spray chamber can be proximate to one another. The spray chamber can include a drain ridge, which can project into an interior of the spray chamber, be depressed away from an interior of the spray chamber, and/or include a treated surface. The spray chamber can also include an output port having a treated surface. In some embodiments, the output port can include an additional port so that rinse liquid can flow through the spray chamber (e.g., continuously and/or intermittently).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures.

FIG. 1 is an exploded front elevation view of a system including a nebulizer and a spray chamber configured to be in fluid communication with the nebulizer (e.g., via a connector), where the tip of the nebulizer and/or an interior of the spray chamber can have a treated surface in accordance with example embodiments of the present disclosure.

FIG. 2 is an isometric view of a spray chamber including a drain and a chamber defining a drain ridge extending toward the drain in accordance with an example embodiment of the present disclosure.

FIG. 3 is a front elevation view of the spray chamber illustrated in FIG. 2.

FIG. 4 is a partial cross-sectional top plan view of the spray chamber illustrated in FIG. 3.

FIG. 5 is top plan view of the spray chamber illustrated in FIG. 2.

FIG. 6 is a partial cross-sectional front elevation view of the spray chamber illustrated in FIG. 5.

FIG. 7 is a partial cross-sectional side elevation view of the spray chamber illustrated in FIG. 5.

FIG. 8 is a bottom plan view of the spray chamber illustrated in FIG. 2.

FIG. 9 is a partial cross-sectional side elevation view of the spray chamber illustrated in FIG. 8.

DETAILED DESCRIPTION

Referring generally to FIGS. 1 through 9, a system 100 can include a nebulizer 102 and a spray chamber 104 configured to be in fluid communication with the nebulizer 102. For instance, the nebulizer 102 and the spray chamber 104 can be connected together using a connector 106 (e.g., a screw-on connector) so that the nebulizer 102 extends into the spray chamber 104 toward the chamber interior. In some embodiments, the nebulizer 102 and/or the spray chamber 104 can be formed of one or more materials, including, but not necessarily limited to: glass, quartz, a polytetrafluoroethylene (PTFE) (e.g., Teflon), and so forth. In embodiments of the disclosure, the nebulizer 102 and/or the spray chamber 104 can be treated to create one or more surfaces that reduce the surface tension of sample liquid waste to reduce or prevent droplet formation (e.g., on the nebulizer). For example, the nebulizer 102 can include a body 108 and a tip 110 protruding from the body 108. In some embodiments, the tip 110 of the nebulizer 102 can have a treated surface 112. For example, the tip 110 of the nebulizer 102 can be frosted, treated using a physical abrasion technique (e.g., sandblasting, laser ablation, etc.), chemically etched, and so forth. One or more interior surfaces of the spray chamber 104 can also be treated (e.g., as previously described). In some embodiments, the entire internal surface portion of the spray chamber 104 can be treated.

In some embodiments, the spray chamber 104 can be a cyclonic spray chamber for receiving an aerosol and conditioning the aerosol to separate a first conditioned portion of the aerosol from a second portion of the aerosol. The spray chamber 104 can include a drain 114 and a chamber 116 defining a drain ridge 118 extending toward the drain 114. In some embodiments, the drain ridge 118 can project into the internal spray chamber (e.g., as a physically positive ridge). In other embodiments, the drain ridge 118 can be depressed away from the internal spray chamber (e.g., as a physically negative ridge, as shown in FIGS. 2 through 9). In some embodiments, the drain ridge 118 of the spray chamber 104 can have a treated surface 120. For instance, the drain ridge 118 of the spray chamber 104 can be frosted, treated using a physical abrasion technique (e.g., sandblasting, laser ablation, etc.), chemically etched, and so forth. It should be noted that while, in some embodiments, the drain ridge 118 may be a physical ridge (which may be treated), in other embodiments, a drain ridge may not necessarily be a physical ridge, and may be formed solely by treating an interior surface of the spray chamber 104 (e.g., where a drain ridge comprises only a chemically treated surface leading waste to the drain 114).

The spray chamber 104 can include an input port 122 in fluid communication with the chamber interior. For example, the input port 122 can be coupled with the nebulizer 102 using the connector 106, which can be screwed onto the spray chamber 104 to retain the nebulizer 102 so that the tip 110 of the nebulizer 102 extends into the spray chamber 104 toward the chamber interior. In some embodiments, the input port 122 of the spray chamber 104 can have a treated surface 124. For instance, an interior surface of the input port 122 can be frosted, treated using a physical abrasion technique (e.g., sandblasting, laser ablation, etc.), chemically etched, and so forth. In embodiments of the disclosure, treated surfaces of the nebulizer 102 and the spray chamber 104 (e.g., the treated surface 112 of the tip 110 of the nebulizer 102, and the treated surface 120 of the drain ridge 118 and/or the treated surface 124 of the input port 122) can be proximate to one another to allow liquid waste from the nebulizer 102 to sheet along the nebulizer surface to waste without forming beaded droplets of liquid (e.g., liquid beads).

In some embodiments, the spray chamber 104 can define an output port comprising an arm 126 located at a vertical (e.g., top) end of the spray chamber 104. In some embodiments, the arm 126 can also comprise a treated surface 128. For instance, an interior of the arm 126 can be frosted, treated using a physical abrasion technique (e.g., sandblasting, laser ablation, etc.), chemically etched, and so forth. In some embodiments, the arm 126 can include an additional port 130 defined by the spray chamber 104 so that rinse liquid can flow over the tip 110 of the nebulizer 102 and through the spray chamber 104 to provide complete rinsing of sample waste (e.g., from previous samples). In this manner, systems and techniques in accordance with the present disclosure can provide washout without, for example, trailing effects. For example, rinse liquid can flow through the spray chamber 104 continuously, substantially continuously, intermittently (e.g., between the analysis of two samples), and so forth. The spray chamber 104 may also include a baffle 132. In operation, larger particles that collide with the walls of the chamber are drained from the chamber, whereas smaller particles are expelled from the chamber through the arm 126. The baffle 128 can serve as an additional region of impact for larger particles in the chamber interior.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A treated nebulizer and spray chamber system comprising:
   a nebulizer having a tip; and
   a monolithic spray chamber assembly comprising:
      a spray chamber,
      an input port,
      an output port perpendicular to the input port and including an inlet portion protruding into the spray chamber,
      a drain extending from an interior bottom surface of the spray chamber that slopes from the input port to the drain, and
      a drain ridge that projects into an interior of the spray chamber and extends toward the drain along the sloped interior bottom surface of the spray chamber,
   at least one of the tip of the nebulizer or the interior of the spray chamber having a treated surface to reduce surface tension of a liquid when the liquid is in contact with the treated surface,
   wherein the spray chamber is configured to be in fluid communication with the nebulizer when the nebulizer is extended into the spray chamber.

2. The system as recited in claim 1, wherein an entirety of the interior of the spray chamber is treated.

3. The system as recited in claim 1, wherein the at least one of the tip of the nebulizer or the interior of the spray chamber is treated using a physical abrasion technique.

4. The system as recited in claim 1, wherein the at least one of the tip of the nebulizer or the interior of the spray chamber is chemically etched.

5. The system as recited in claim 1, wherein the tip of the nebulizer and the interior of the spray chamber each include a treated surface.

6. The system as recited in claim 5, wherein the treated surfaces of the tip of the nebulizer and the interior of the spray chamber are proximate to one another when the nebulizer is extended into the spray chamber.

7. The system as recited in claim 1, wherein the drain ridge is depressed away from an interior of the spray chamber.

8. The system as recited in claim 1, wherein the drain ridge comprises the treated surface.

9. The system as recited in claim 1, wherein the drain ridge comprises only the treated surface.

10. The system as recited in claim 1, wherein the output port comprises the treated surface.

11. The system as recited in claim 1, wherein the output port comprises an additional port so that rinse liquid can flow over the tip of the nebulizer and through the spray chamber.

12. The system as recited in claim 11, wherein the rinse liquid can flow continuously.

13. The system as recited in claim 11, wherein the rinse liquid can flow intermittently.

* * * * *